United States Patent
Rosengart et al.

(10) Patent No.: US 6,508,802 B1
(45) Date of Patent: Jan. 21, 2003

(54) REMOTE SENSING GENE THERAPY DELIVERY DEVICE AND METHOD OF ADMINISTERING A THERAPEUTIC SOLUTION TO A HEART

(75) Inventors: Todd K. Rosengart, Highland Park, IL (US); Ronald G. Crystal, Potomac, MD (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/576,752

(22) Filed: May 23, 2000

(51) Int. Cl.$^7$ .............................................. A61M 25/00
(52) U.S. Cl. .................. 604/523; 604/528; 604/164.01; 604/181; 604/187; 604/218; 604/272
(58) Field of Search ................................. 604/523, 528, 604/164.01, 116, 117, 181, 187, 95.04, 1, 207, 208, 218, 246, 264, 272

(56) References Cited

U.S. PATENT DOCUMENTS

| | | | |
|---|---|---|---|
| 510,413 | A | 12/1893 | Dolge |
| 2,402,306 | A | 6/1946 | Turkel |
| 2,498,692 | A | 2/1950 | Mains |
| 2,512,568 | A | 6/1950 | Saffir |
| 2,551,902 | A | 5/1951 | Rieck |
| 2,670,673 | A | 3/1954 | Gordon et al. |
| 2,688,329 | A | 9/1954 | Wallace |
| 2,700,385 | A | 1/1955 | Ortiz |
| 2,952,256 | A | 9/1960 | Meader et al. |
| 3,435,824 | A | 4/1969 | Gamponia |
| 3,467,096 | A | 9/1969 | Horn |
| 3,487,837 | A | 1/1970 | Petersen |
| 3,530,492 | A | 9/1970 | Ferber |
| 3,572,336 | A | 3/1971 | Hershberg |
| 3,595,231 | A | 7/1971 | Pistor |
| 3,765,420 | A | 10/1973 | Felczak |
| 3,783,876 | A | 1/1974 | Dye |
| 3,797,491 | A | 3/1974 | Hurschman |
| 3,826,241 | A | 7/1974 | Bucalo |
| 3,831,584 | A | 8/1974 | Bucalo |
| 3,920,001 | A | 11/1975 | Edwards |
| 3,951,132 | A | 4/1976 | Bucalo |
| 3,991,767 | A | 11/1976 | Miller |

(List continued on next page.)

FOREIGN PATENT DOCUMENTS

| | | |
|---|---|---|
| DE | 3920707 A | 1/1991 |
| WO | WO 99/04851 A | 2/1999 |
| WO | WO 99/44656 A1 | 9/1999 |

*Primary Examiner*—Teresa Walberg
*Assistant Examiner*—Fadi H. Dahbour
(74) *Attorney, Agent, or Firm*—Leydig, Voit & Mayer, Ltd.

(57) ABSTRACT

The invention provides a steerable device for the delivery of a therapeutic solution, in particular, an angiogenesis-promoting substance into a heart, and a method of delivering such a substance into the heart. The device includes an elongated needle which the physician may steer by asserting a tensioning force on a steering cable coupled to the needle toward its distal end. A axially-slidable steering sleeve is disposed about the needle and the steering cable, and the position of the steering sleeve may be adjusted to control the radius of flexure of the needle. The needle body is flexible enough to maneuver around thoracic and cardiac geometry, yet sufficiently rigid to facilitate such maneuvering. The needle may also have a stop, or platform, spaced from the distal needle tip to stabilize the needle in the cardiac tissue. According to a method of the invention, the needle may be inserted into the heart tissue through lung tissue adhering to the heart, as is common in re-operative patients. The platform may either transit the needle as the platform contacts the lung or heart tissue, or the platform may move forward to contact tissue as needle contact with heart tissue is confirmed.

40 Claims, 7 Drawing Sheets

U.S. PATENT DOCUMENTS

| | | |
|---|---|---|
| 4,150,669 A | 4/1979 | Lattore |
| 4,167,179 A | 9/1979 | Kirsch |
| 4,168,708 A | 9/1979 | Lepley |
| 4,222,380 A | 9/1980 | Terayama |
| 4,230,119 A | 10/1980 | Blum |
| 4,243,035 A | 1/1981 | Barrett |
| 4,245,624 A | 1/1981 | Komiya |
| 4,280,508 A | 7/1981 | Barrada |
| 4,299,230 A | 11/1981 | Kubota |
| 4,356,826 A | 11/1982 | Kubota |
| 4,419,094 A | 12/1983 | Patel |
| 4,578,061 A | 3/1986 | Lemelson |
| 4,645,495 A | 2/1987 | Vaillancourt |
| 4,674,506 A | 6/1987 | Alcond |
| 4,721,109 A | 1/1988 | Healey |
| 4,753,236 A | 6/1988 | Healey |
| 4,760,847 A | 8/1988 | Vaillancourt |
| 4,787,891 A | 11/1988 | Levin et al. |
| 4,798,193 A | 1/1989 | Giesy et al. |
| 4,838,851 A | 6/1989 | Kuzmanovich |
| 4,861,336 A | 8/1989 | Helzel |
| 4,877,037 A | 10/1989 | Ko et al. |
| 4,919,653 A | 4/1990 | Martinez et al. |
| 4,932,421 A | 6/1990 | Kaali et al. |
| 4,940,458 A | 7/1990 | Cohn |
| 4,946,442 A | 8/1990 | Sanagi |
| 4,946,463 A | 8/1990 | Wright |
| 4,966,589 A | 10/1990 | Kaufman |
| 4,976,688 A | 12/1990 | Rosenblum |
| 4,994,041 A | 2/1991 | Dombrowski et al. |
| 5,036,868 A | 8/1991 | Berggren |
| 5,037,428 A | 8/1991 | Picha |
| 5,080,104 A | 1/1992 | Marks et al. |
| 5,098,412 A | 3/1992 | Shiu |
| 5,121,750 A | 6/1992 | Katims |
| 5,146,913 A | 9/1992 | Khorsandian |
| 5,147,307 A | 9/1992 | Gluck |
| 5,192,270 A | 3/1993 | Carswell, Jr. |
| 5,192,289 A | 3/1993 | Jessen |
| 5,195,526 A | 3/1993 | Michelson |
| 5,254,088 A | 10/1993 | Lundquist et al. |
| 5,259,377 A | 11/1993 | Schroeder |
| 5,261,889 A | 11/1993 | Laine et al. |
| 5,269,754 A | 12/1993 | Rydell |
| 5,273,525 A | 12/1993 | Hofmann |
| 5,290,258 A | 3/1994 | Ennis, III et al. |
| 5,312,351 A | 5/1994 | Gerrone |
| 5,322,510 A | 6/1994 | Lindner et al. |
| 5,323,789 A | 6/1994 | Berggren |
| 5,335,670 A | 8/1994 | Fishman |
| 5,336,182 A | 8/1994 | Lundquist et al. |
| 5,354,279 A | 10/1994 | Höfling |
| 5,364,374 A | 11/1994 | Morrison et al. |
| 5,376,084 A | 12/1994 | Bacich et al. |
| 5,380,292 A | 1/1995 | Wilson |
| 5,395,327 A | 3/1995 | Lundquist et al. |
| 5,417,662 A | 5/1995 | Hjertman et al. |
| 5,417,683 A | 5/1995 | Shiao |
| 5,425,739 A | 6/1995 | Jessen |
| 5,441,499 A | 8/1995 | Fritzsch |
| 5,464,395 A | 11/1995 | Faxon et al. |
| 5,478,315 A | 12/1995 | Brothers et al. |
| 5,478,330 A | 12/1995 | Imran et al. |
| 5,520,650 A | 5/1996 | Zadini et al. |
| 5,522,815 A | 6/1996 | Durgin, Jr. et al. |
| 5,531,686 A | 7/1996 | Lundquist et al. |
| 5,536,251 A | 7/1996 | Evard et al. |
| 5,569,217 A | 10/1996 | Luther |
| 5,569,237 A | 10/1996 | Beckenstein |
| 5,611,778 A | 3/1997 | Brinon |
| 5,673,704 A | 10/1997 | Marchlinski et al. |
| 5,674,197 A | 10/1997 | Van Muiden et al. |
| 5,713,890 A | 2/1998 | Chasan |
| 5,810,757 A | 9/1998 | Sweezer, Jr. et al. |
| 5,820,591 A | 10/1998 | Thompson et al. |
| 5,820,592 A | 10/1998 | Hammerslag |
| 5,827,216 A | 10/1998 | Igo et al. |
| 5,845,646 A | 12/1998 | Lemelson |
| 5,846,225 A | 12/1998 | Rosengart et al. |
| 5,868,764 A | 2/1999 | Rosengart |
| 5,882,331 A | 3/1999 | Sasaki |
| 5,997,509 A | 12/1999 | Rosengart et al. |
| 6,027,473 A * | 2/2000 | Ponzi .......................... 604/528 |
| 6,033,378 A * | 3/2000 | Lundquist et al. .......... 604/528 |
| 6,120,476 A * | 9/2000 | Fung et al. ............... 604/95.04 |
| 6,126,633 A * | 10/2000 | Kaji et al. ................ 604/95.04 |
| 6,171,277 B1 * | 1/2001 | Ponzi ....................... 604/95.04 |
| 6,179,809 B1 * | 1/2001 | Khairkhahan et al. ... 604/95.04 |
| 6,183,463 B1 * | 2/2001 | Webster, Jr. ................ 604/528 |
| 6,203,525 B1 * | 3/2001 | Whayne et al. ............. 604/528 |
| 6,277,107 B1 * | 8/2001 | Lurie et al. .................. 604/528 |
| 6,332,880 B1 * | 12/2001 | Yang et al. .................. 604/528 |
| 6,346,099 B1 * | 2/2002 | Altman ........................ 604/528 |

\* cited by examiner

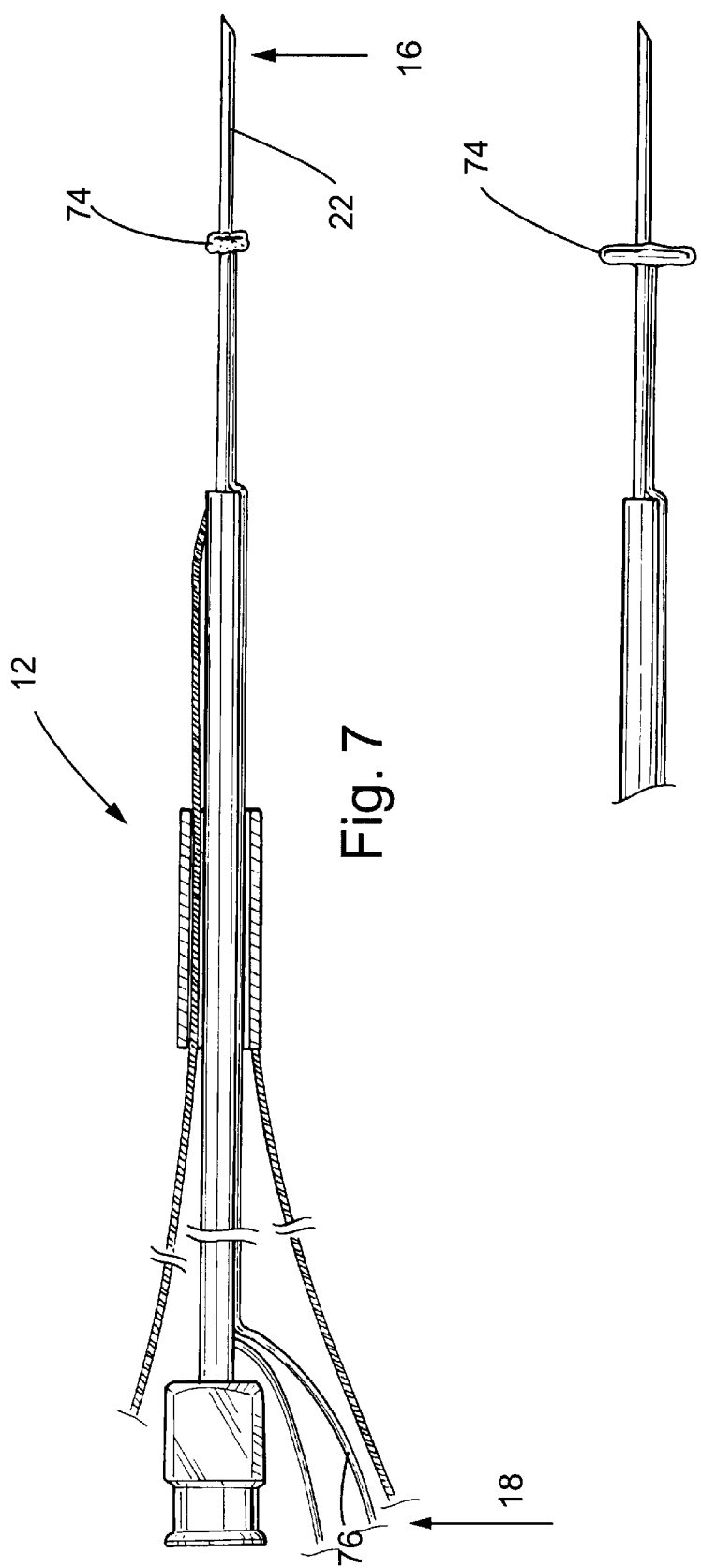

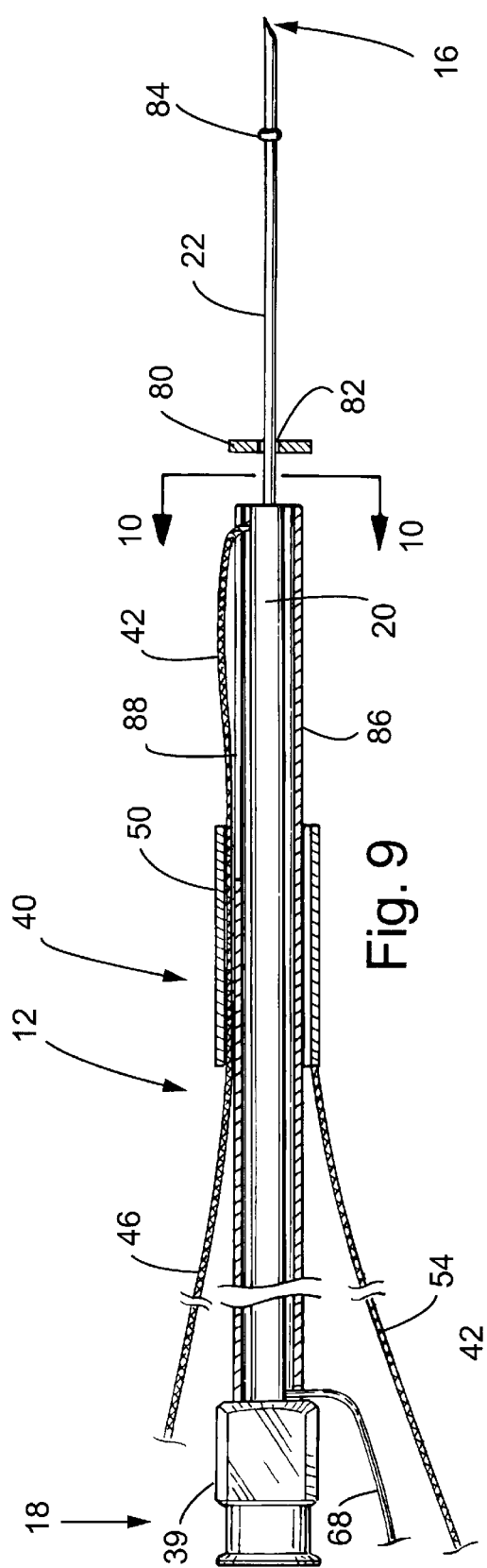
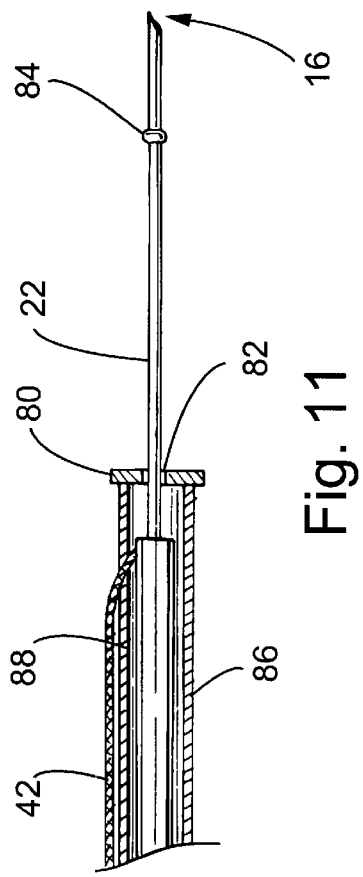
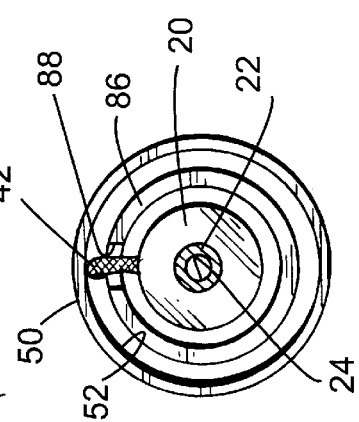
Fig. 9
Fig. 11
Fig. 10

REMOTE SENSING GENE THERAPY DELIVERY DEVICE AND METHOD OF ADMINISTERING A THERAPEUTIC SOLUTION TO A HEART

FIELD OF THE INVENTION

The invention relates to devices and methods for delivering a therapeutic solution, and more specifically to a steerable needle and a method for delivering an angiogenic substance into a beating heart.

BACKGROUND OF THE INVENTION

There have been numerous recent advances in therapies such as angioplasty and coronary bypass surgery, which are now commonly used in the treatment of ischemic heart disease. There still exist a significant number of patients for whom these conventional therapies are not feasible options in a number of circumstances. For example, conventional coronary bypass surgery is not a treatment option in patients with diffuse small vessel coronary artery disease due to the small size and large number of diseased vessel segments. Further, re-occlusion of a diseased vessel may occur despite multiple angioplastic procedures or bypass surgeries.

One promising alternative treatment for ischemic heart disease is the delivery of angiogenesis-promoting substances to the heart tissue to induce angiogenesis. Angiogenesis is a complex biological process that results in the growth of new blood vessels within tissue. Angiogenesis is an essential process common to several normal and pathologic conditions including embryologic development, wound healing, development of neoplasms, and the like. Angiogenesis involves the disruption of vascular basement membranes, migration and proliferation of endothelial cells, and subsequent blood vessel formation and maturation.

Angiogenesis has also been induced in heart tissue for reperfusion of tissue compromised by myocardial ischemia. Several growth factors or mediators are known to elicit angiogenic responses, and administration of these mediators promotes revascularization of ischemic tissues. These growth factors are typically proteins which stimulate endothelial cell reproduction in the target tissue. Vascular endothelial growth factor (VEGF) is one of the most specific of the known angiogenic mediators due to localization of its receptors almost exclusively on endothelial cells. Receptors for VEGF are upregulated under ischemic conditions. Accordingly, the administration of VEGF augments the development of collateral vessels and improves function in peripheral and myocardial ischemic tissue.

Delivery of VEGF remains a significant challenge. The half-life of VEGF is very short. Accordingly, the tissue must be exposed to the growth factor for a period of days. The administration of high doses of VEGF, however, is associated with hypotension.

The systemic administration of VEGF can induce angiogenesis in tissues other than that which has been targeted, such as occult tumors, or sensitive diseased organs, such as the retina. This promiscuous induction of angiogenesis can cause blindness, increase the aggressiveness of tumor cells, and lead to a multitude of other negative side-effects. Accordingly, the growth factor should be limited to the target tissue.

The growth factor can be delivered to the target tissue through the use of indwelling catheters over a period of time. A preferred method of delivering the growth factor, however, is in the form of gene transfer, for example, by a replication deficient adenoviral vector containing the transgene coding for the growth factor. Under this method, a quantity of the adenoviral vector having the desired genetic component is delivered to the treatment area by injection in solution.

In the past, an open-chest procedure has been used to deliver the treatment solution. According to this procedure, the patient's chest is opened surgically to expose the heart. The solution containing the adenoviral vector is then delivered to the heart tissue by using a syringe to make a number of injections in a grid-like pattern, with the surgeon keeping track of the location of each injection. International Patent Application WO 98/32859 discloses a method of enhancing the level of perfusion of blood to a target tissue during such procedure.

Once injected, the adenoviral vector causes the cells in the target tissue to produce the desired growth factor, and this growth factor production of the treated cells will continue for a period of time. Previous studies have shown the feasibility and efficacy of safe, sustained, and localized expression of angiogenesis-promoting growth factors utilizing adenoviral-mediated gene transfer therapy.

It is desirable to be able to provide the above described therapy without the necessity of performing open-chest surgery on the patient. U.S. Pat. No. 5,997,509 discloses an injection apparatus and method for providing gene therapy treatment to the heart or other internal organs without necessitating such open heart surgery. A procedure for utilizing a device also is disclosed in International Patent Application WO 99/44656. According to the procedure, the patient's lung is partially collapsed to enable access to areas of the heart. The therapeutic substance may be injected into the patient's myocardium by passing the needle directly through the patient's pericardium.

The device disclosed in the '509 patent and International Patent Application WO 99/44656 includes an elongate flexible tubular body having a hollow needle mounted at the distal end for delivery of the therapeutic substance to the tissue. This and other currently available devices have relatively complex designs, and, accordingly, are extremely expensive to manufacture. Further, they may be difficult to manipulate around the contours of the heart or to ensure stability of the needle against the target cardiac tissue.

Additionally, access to the target cardiac tissue is often obscured by other organs and tissues. One or more retractors may be used in order to physically move the obscuring organs or tissues in order to gain access to the cardiac tissue. A grasping type of retractor, a mechanically expandable retractor, an inflatable retractor, or another type of retractor known in the art may be utilized as disclosed, for example, in International Patent Application WO 99/44656. In reoperative patients, however, lung tissue frequently adheres directly to the cardiac tissue. Under these conditions, the lung and cardiac tissues cannot typically be separated by conventional methods without damage to either or both of the organs. As a result, retraction devices such as those disclosed in the '509 patent and International Patent Application WO 99/44656 are not readily utilized under such circumstances.

BRIEF SUMMARY OF THE INVENTION

The present invention provides a method and a minimally invasive injection device which is steerable such that it may be maneuvered into a desired position for administering an injection. The device includes a hollow needle which is adapted for connection to a solution supply. The needle has an elongated flexible body with a sharpened tip at its distal end for penetration into tissue. The needle may be steered by means of a steering cable and a moveable steering sleeve.

The steering cable is an elongated cable or wire which is coupled to the needle toward its distal end and extends substantially the length of the needle to its proximal end. The user may exert a tensioning force on the steering cable to cause the elongated flexible body of the needle to flex or arch along a flexion radius. The moveable steering sleeve is slideably disposed along the elongated flexible body with the steering cable extending through the steering sleeve. Accordingly, by moving the steering sleeve axially along the needle, the user can adjust the flexion radius of the needle. That is, the needle body will be substantially straight from its proximal end up to and including the section extending through the steering sleeve. As a tension force is exerted on the steering cable, however, the needle body distal the steering sleeve will flex or arch, moving the needle tip toward the proximal end of the needle. The steering sleeve may be slid along the needle by means of a sufficiently rigid steering sleeve adjustment cable, which likewise extends toward and can be operated from the proximal end of the needle. Thus, the device provides a simplified, steerable needle arrangement that may be efficiently and economically produced.

A device constructed according to teachings of the invention can be easily controlled and efficiently maneuvered within a body cavity, the flexible needle contouring to cardiac and thoracic geometry to properly position the needle tip and administer the injection. Accordingly, the device may readily be utilized in minimally invasive procedures to deliver angiogenesis-promoting substances from a remote location to an area of ischemic heart tissue without necessitating open-chest surgery.

The delivery of the therapeutic substance to the myocardium can be by way of any suitable route, transpericardially, as well as endocardially. While the device may be utilized during open-heart surgery, or advanced into the heart through any artery, including, for example, the femoral artery, the device may also be utilized in the manner disclosed in International Patent Application WO 99/44656. More specifically, the patient's lung may be partially collapsed by the introduction of gas into the patient's thoracic cavity. This enlarges the working area for injection of the therapeutic substance and increases access to heart tissue.

According to other features of the invention, various methods of delivering a therapeutic substance are disclosed. One such method includes the steps of inserting an elongated device body into a body cavity through an opening, and using the steering cable, and the steering sleeve adjustment cable and steering sleeve to steer the body distal end within the cavity. Another method further includes the steps of inserting the device into the patient's thoracic cavity through an opening the patient's chest wall, passing a needle into the heart tissue and delivering the therapeutic substance. Further, the needle may be passed directly into the chest cavity in a true percutaneous technique wherein no incision is made. Under these circumstances, the opening in the chest is limited only the diameter of the device or a small trocar.

Inasmuch as access to cardiac tissue is often limited in re-operative patients, however, the invention further includes a methods of administering the therapeutic solution when lung tissue adhering to the heart obscures access. According to the method, the needle is passed directly through the patient's lung tissue and into the heart tissue.

According to another method, the device is stabilized against the tissue by means of a moveable stabilizing platform which is disposed either against the lung tissue or against the pericardium.

According to one design, the stabilizing platform is spaced from the distal tip of the needle and can transit the needle tip a sufficient distance to allow the needle tip to penetrate and pass through the lung tissue, and to penetrate the heart tissue to a desired depth. The distal-most position of the movable platform is preferably the optimum cardiac tissue penetration depth. The movable platform may be retained on the needle tip by a stop along the needle tip, or any other appropriate structure or means. According to a preferred embodiment, the platform can transit the needle tip from a position approximately 5–10 mm from the distal tip to approximately 35–50 mm proximal the distal tip. In this way, the needle tip can penetrate and extend through the lung tissue, and then penetrate the cardiac tissue a desired depth to administer the therapeutic solution.

According to another feature of the invention, the platform may be stopped, advanced to, or disposed at a desired position to provide the optimum cardiac tissue penetration when cardiac penetration has been confirmed via an ECG signal. An electrode is preferably located on the on the distal tip of the needle, and connected to an ECG. In this way, the surgeon can determine when the needle has penetrated the patient's myocardium and is properly positioned. Penetration of the myocardium by the needle will show as a current injury on the ECG.

By way of further example, the moveable platform may be in the form of an inflatable balloon which may be inflated to a desired volume once cardiac contact has been confirmed. Inflation may be accomplished by means of a gas line extending along the length of the needle body between the platform and an appropriate gas source. The platform of this design is preferably disposed along the needle tip at a given axial position which defines the optimum cardiac penetration depth. The deflated platform may be passed through the lung tissue and then inflated adjacent the heart tissue when proper placement has been confirmed. Other platform designs such as a spring-biased platform may be provided.

These and other features and advantages of the invention will be more readily apparent upon reading the following description of a preferred exemplified embodiment of the invention and upon reference to the accompanying drawings.

BRIEF DESCRIPTION OF THE DRAWINGS

FIG. 7 is an enlarged plan view of a third embodiment of the invention, a portion of the components being shown in cross-section.

FIG. 8 is a fragmentary view of the device of FIG. 7 wherein the platform is inflated.

FIG. 9 is an enlarged plan view of an alternate embodiment of the invention, a portion of the components being shown in cross-section.

FIG. 10 is a cross-sectional view of the device of FIG. 7 taken along line 10—10 in FIG. 9.

FIG. 11 is a fragmentary, partial cross-sectional view of the device of FIG. 9 wherein the platform adjustment sleeve is moved to advance the platform along the needle tip.

While the invention will be described in connection with certain preferred embodiments, there is no intent to limit it to those embodiments. On the contrary, the intent is to cover all alternatives, modifications, and equivalents included within the spirit and scope of the invention as defined by the appended claims.

DESCRIPTION OF THE PREFERRED EMBODIMENT

Figure 1:
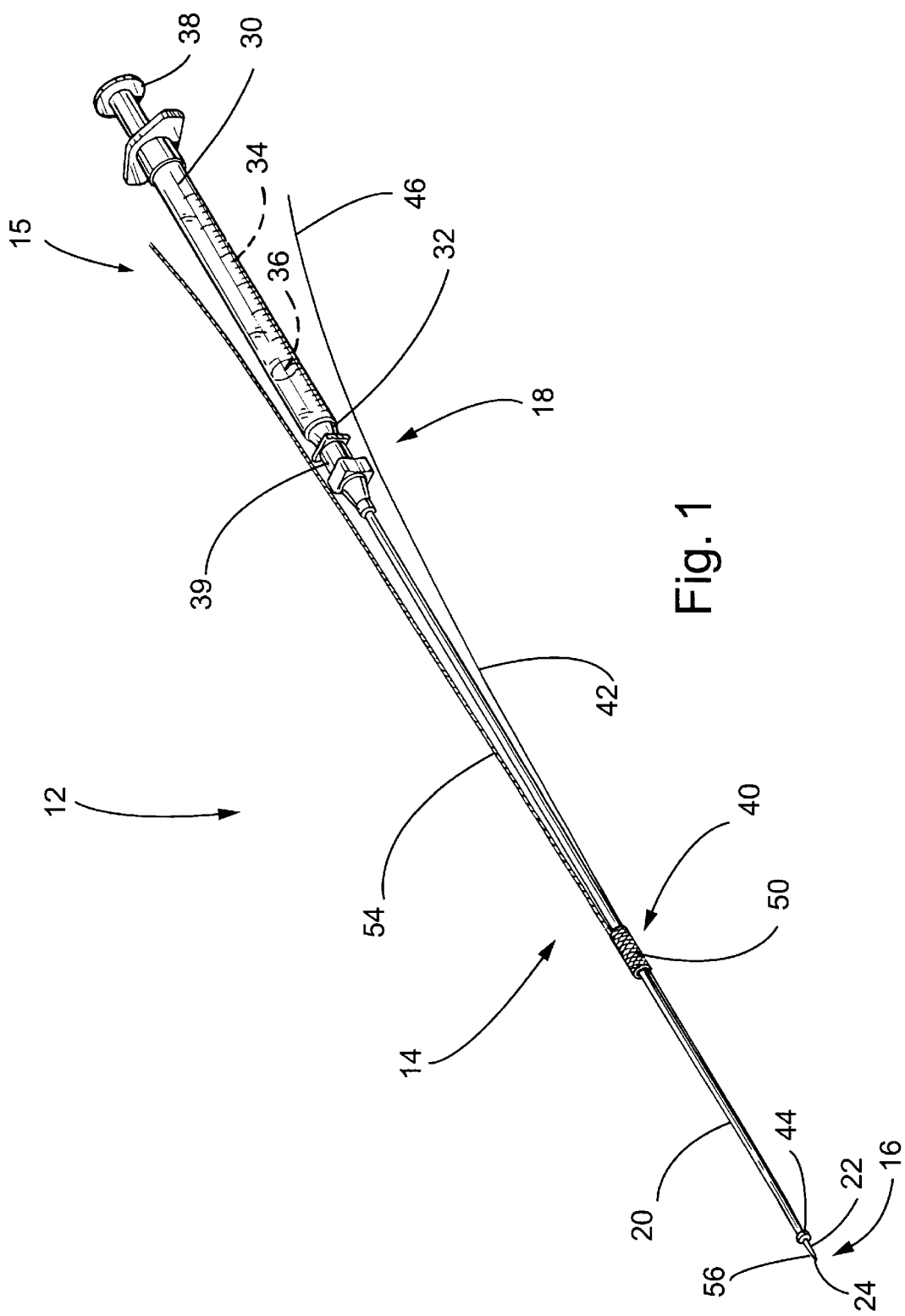
FIG. 1 is a plan view of a delivery device constructed in accordance with teachings of the invention in conjunction with a syringe.

There is shown in FIG. 1 a delivery device 12 constructed in accordance with teachings of the invention for use in delivering a therapeutic solution to the tissue of a heart, especially a beating heart. The device 12 includes a needle assembly 14 adapted to be coupled to a syringe or other solution supply device 15. The distal end of the needle assembly 14 is designated generally as 16 and the proximal end is designated as 18. The needle assembly 14 includes an elongated body or cannula 20 with a sharpened needle tip 22 at its distal end. In the embodiment illustrated, the needle tip 22 is of a smaller diameter than the needle body 20. A bore 24 extends through the needle assembly 14 and is in communication with the solution supply device 15. During use, the device 12 may, for example, be inserted through a thoracoscopic port (not shown), giving thoracoscopic access to the patient's heart. The therapeutic solution may then be injected from the solution supply device 12 through the bore 24 of the needle assembly 14 directly into the cardiac tissue in a predetermined quantity.

In the currently preferred embodiment of the invention, the solution supply device is a conventional syringe 15. The syringe 15 includes a hollow cylindrical body 30 having a distal necked-in end 32. A plunger shaft 34 with a plunger 36 mounted on the distal end thereof and a thumb button 38 mounted to the proximal end thereof is slidably disposed within the cylindrical body, the plunger extending outward from the body. During use, the operator may actuate the plunger 36 by depressing the plunger thumb button 38 to deliver the therapeutic solution. The needle assembly 14 may be coupled to the syringe 15 by any appropriate coupling 39. In the currently preferred design, a metal hub 39 is utilized which has a large bore for receiving the distal necked-in end 32 of the syringe 15. The hub 39 further includes a smaller bore which communicates with the large bore and the bore 24 of the needle assembly 14 to establish fluid communication between the syringe 15 and the needle tip 22 for delivery of therapeutic fluid.

While the solution supply device has been explained with regard to a syringe 15, it will be appreciated by those of skill in the art that the supply device can be of any appropriate design. Additionally, the supply device may include any appropriate metering device to control the amount of therapeutic substance injected at the injection site. For example, and as explained in International Patent Application WO 99/44656, the syringe 15 may include a shaft having screw threads or include a ratchet mechanism which permits the plunger button to advance within the cylindrical body only a predetermined distance to permit only a predetermined amount of therapeutic solution to be administered at a given injection site. Alternately, the administration of a controlled amount of the therapeutic solution may be facilitated by a computer controlled device.

Figure 2:
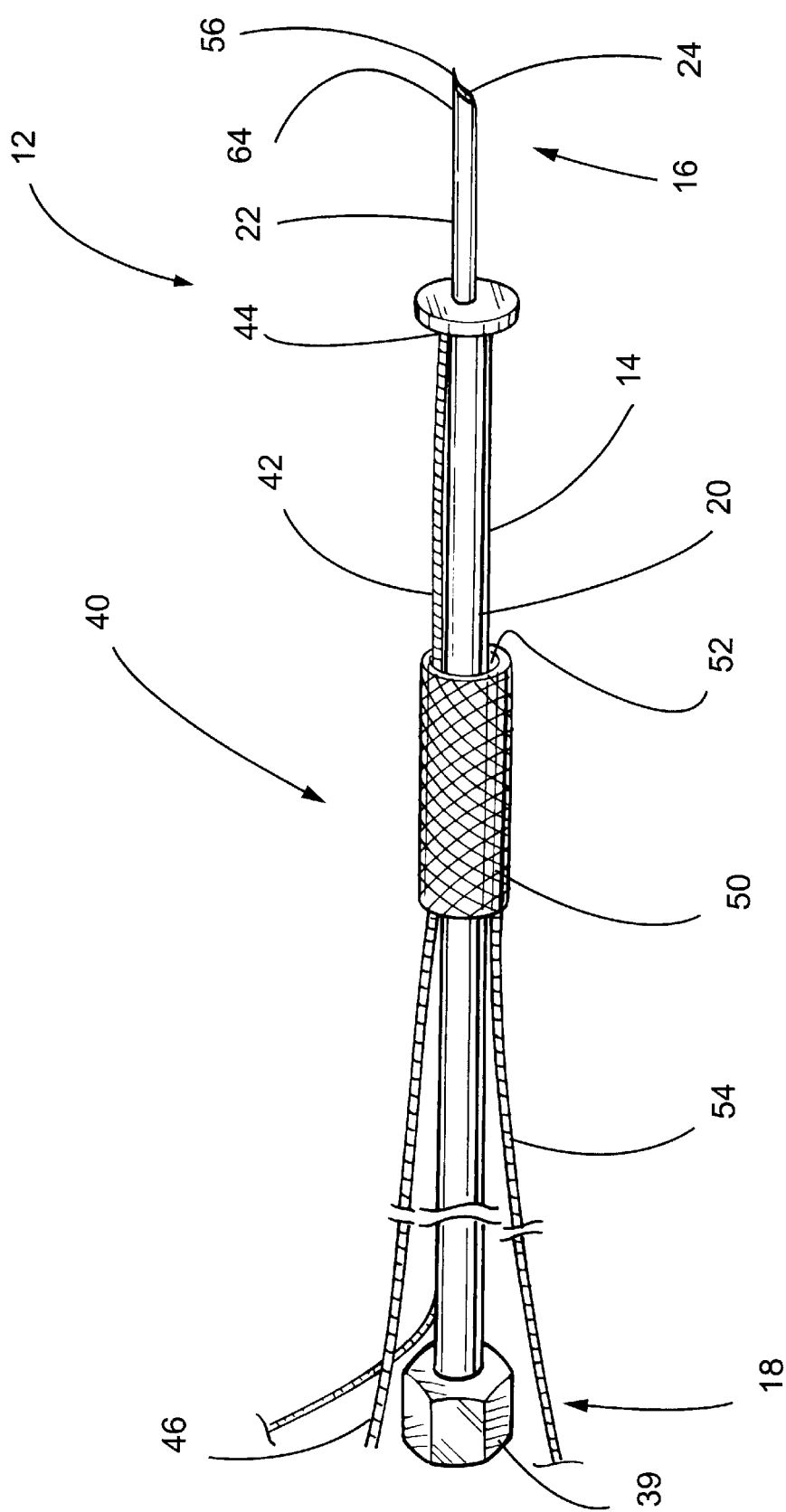
FIG. 2 is a perspective view of a needle assembly of the delivery device of FIG. 1.
Figure 3:
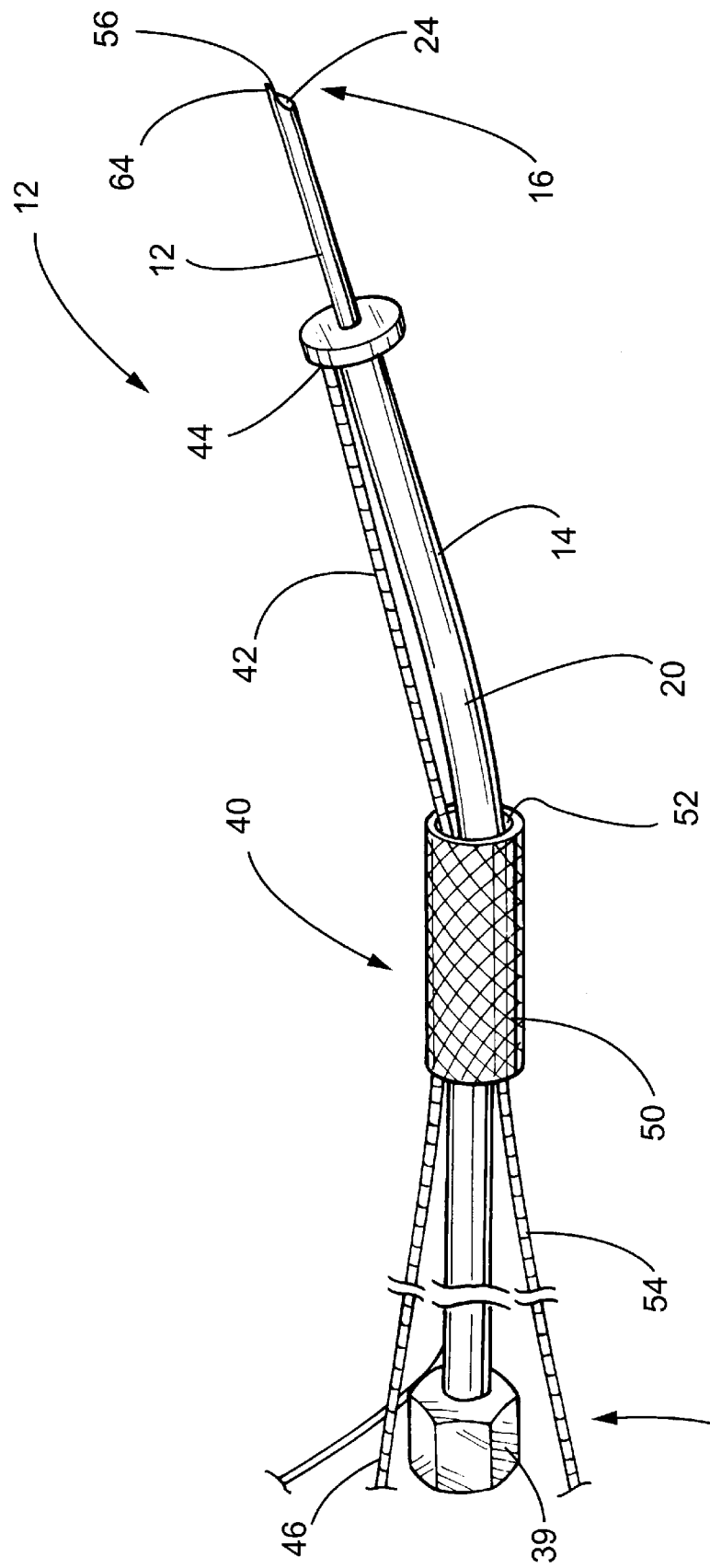
FIG. 3 is a perspective view of the needle of FIG. 2 wherein a tensile force has been applied to the steering cable.
Figure 4:
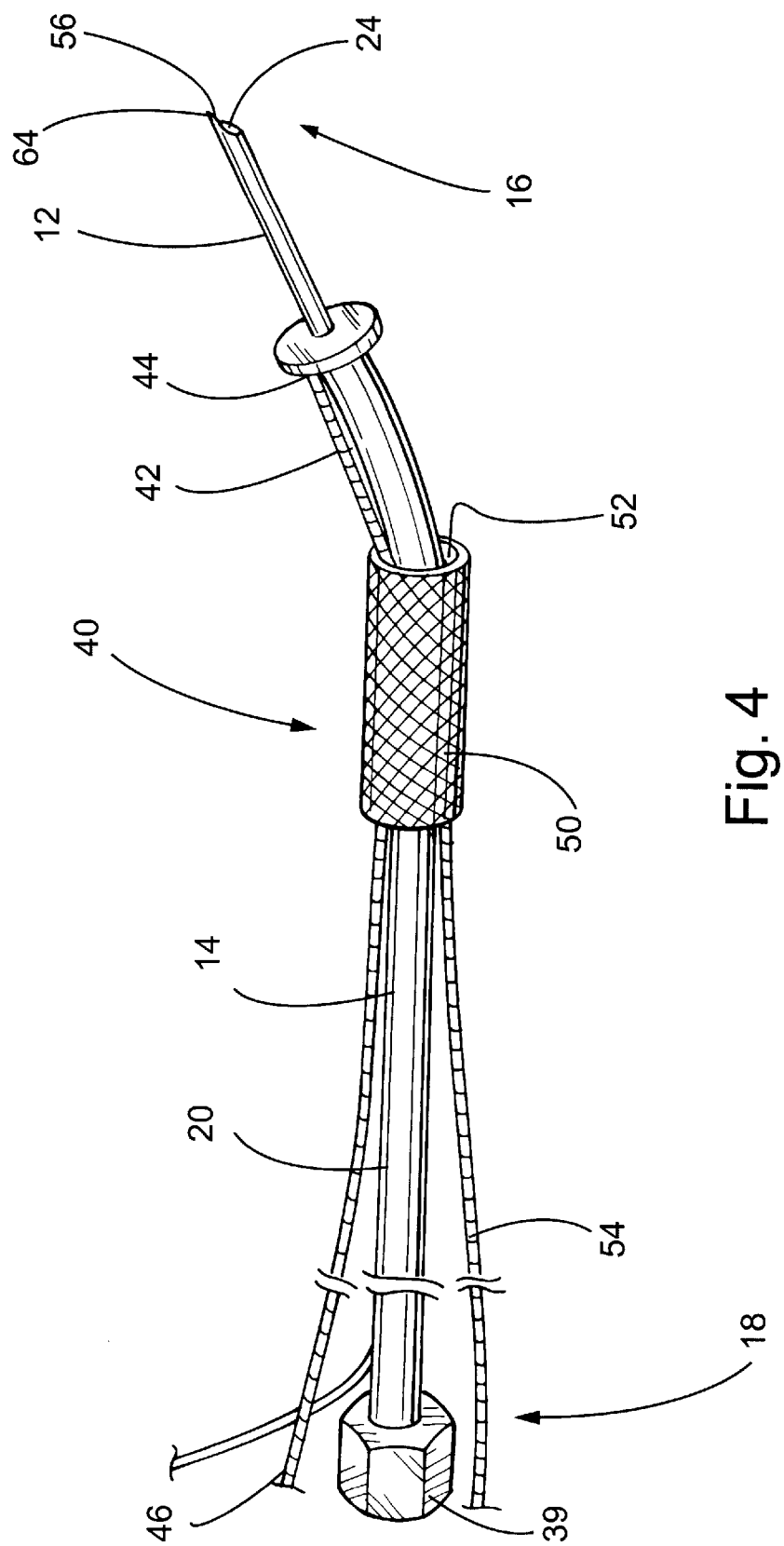
FIG. 4 is a plan view if the needle of FIG. 2 similar to FIG. 3 wherein steering sleeve is alternately positioned and a tensile force has been applied to the steering cable.

In accordance with the invention, the movement of the distal end 16 of the needle assembly 14 may be controlled by a steering mechanism (designated generally as 40). The needle assembly 14 and steering mechanism 40 are enlarged and schematically illustrated in FIGS. 2–4. The steering mechanism includes a steering cable 42 which is coupled to the needle body 20 at a distal attachment 44 toward the distal end 16 of the needle body 20. The steering cable 42 extends toward the proximal end 18 of the needle assembly 14 and substantially the length of the needle assembly 14. It will be appreciated by those of skill in the art that the assertion of a tensioning force on the proximal end 46 of the steering cable 42 flexes or arches the distal end 16 of the needle assembly 14 back towards the proximal end 18 of the needle assembly 14 along a dynamic radius of flexure as shown in FIG. 3. It will be appreciated by those of skill in the art that the needle assembly 14 increasingly arches, that is, the radius of flexure will decrease, as the level of tensioning force on the steering cable 42 is increased.

To further control this radius of flexure and the location of the bend, a moveable steering sleeve 50 is provided. The steering sleeve 50 is essentially a hollow tube having an internal bore 52, which is disposed about the needle body 20 such that the sleeve 50 may slide axially along the needle assembly 14, the steering cable 42 extending through the bore 52. As may be seen in FIGS. 3 and 4, during operation, the length of the needle body 20 which remains straight and the length of the needle assembly 14 which arches is determined by the position of the steering sleeve 50 relative to the distal attachment 44 of the steering cable 42. In this way, the radius of flexure is determined, at least in part, by the position of the steering sleeve 50 as the steering cable 42 is tensioned by the user.

In order to move the steering sleeve 50 in the distal and proximal directions along the needle assembly 14, a steering sleeve adjustment cable 54 is provided. The steering sleeve adjustment cable 54 may be of any appropriate material, so long as it is sufficiently rigid to push the sleeve 50 along needle assembly 14. The currently preferred embodiment comprises a stainless steel cable on the order of 1–3 mm in diameter.

Those of skill in the art will appreciate that the needle body 20 must be sufficiently rigid to support the steering mechanism 40, while being sufficiently flexible to permit the needle body 20 to arch or flex as a tensioning force is applied to the steering cable 42. Further, the needle body 40 must be sufficiently resilient such that it remains biased in a substantially straight position to permit its manipulation and use in successive injections if so desired. The needle assembly 14 portion of the device 12 will typically be approximately 300–400 mm long. A needle body 20 on the order of 20–25 Ga. has been found to be adequately flexible, yet sufficiently rigid to permit proper functioning of the steering mechanism 40 and placement of the needle tip 22.

Inasmuch as the steering mechanism 40 does not act directly upon the needle tip 22, it is not necessary for the needle tip 22 to be as rigid as the needle body 20. Moreover, it is preferable that the needle tip 22 be of a smaller gauge in order to facilitate penetration of the needle tip 22 into body tissue and to minimize extravasation of injectate. It has been determined that a 25–30 Ga. (e.g., 28 Ga.) cannula is particularly appropriate. While the illustrated needle tip 40 includes a bevel sharp tip 56, it will be appreciated that an alternate tip geometry or structure may be provided.

It will be appreciated that the device 12 can be readily constructed from "off-the-shelf" type components so that it may be economically manufactured. Thus, the manufacture is not cost prohibitive, and the device may be utilized as a single use, disposable device.

Figure 5:
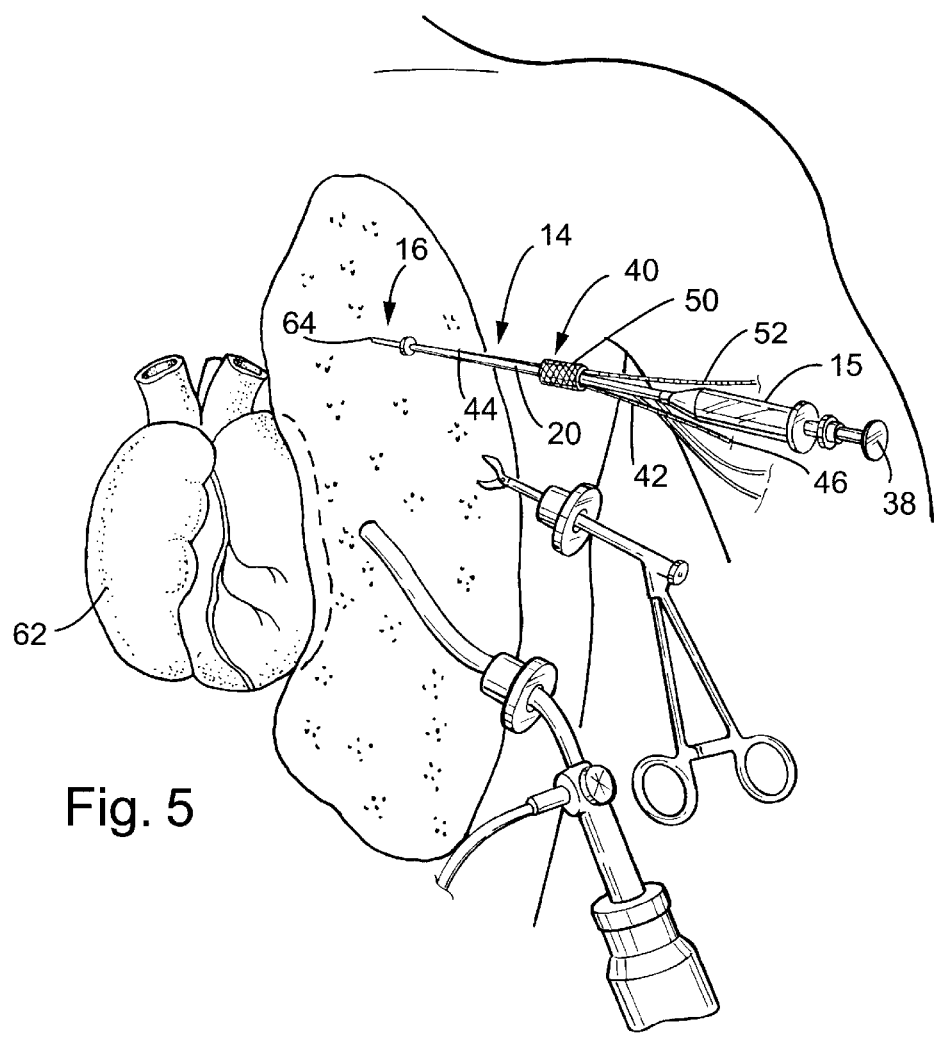
FIG. 5 is a plan view of a patient's chest showing the organs therein and various instruments positioned for a minimally invasive procedure.

During use, the elongated needle body 20 is inserted into the patient's body cavity through an opening. The opening in a true percutaneous technique is the opening formed by the needle assembly 14 itself as it is inserted into the chest wall and through the ribs to the heart. Under these circumstances, the opening is substantially equivalent to the diameter of the device 12. Alternately, the needle may be inserted through a small trocar. If, for example, the device 12 has a diameter of 3 mm, the trocar might have a diameter of 5 mm. The opening might also be in the form of an airtight port 56 in the chest wall as illustrated in FIG. 5 and disclosed, for example in International Patent Application WO 99/44656.

Once inserted, the needle assembly 14 is steered into the desired position using the steering mechanism 40. That is, the physician exerts a tensile force on the proximal end 46 of the steering cable 42, the distal end 44 of the steering cable 42 being coupled to the needle body 20 toward the body distal end 16 to steer the body distal end 16 along a flexion radius. The physician may adjust the flexion radius by locating the steering sleeve 50 at a desired position along the needle body 20 using the steering sleeve adjustment cable 52. Once appropriately positioned, the physician can pass the sharpened needle tip 22 into the heart tissue 62, and depressing the syringe 15 thumb button 38 to advance the plunger 36 and deliver the therapeutic substance to the patient's heart.

Figure 6:
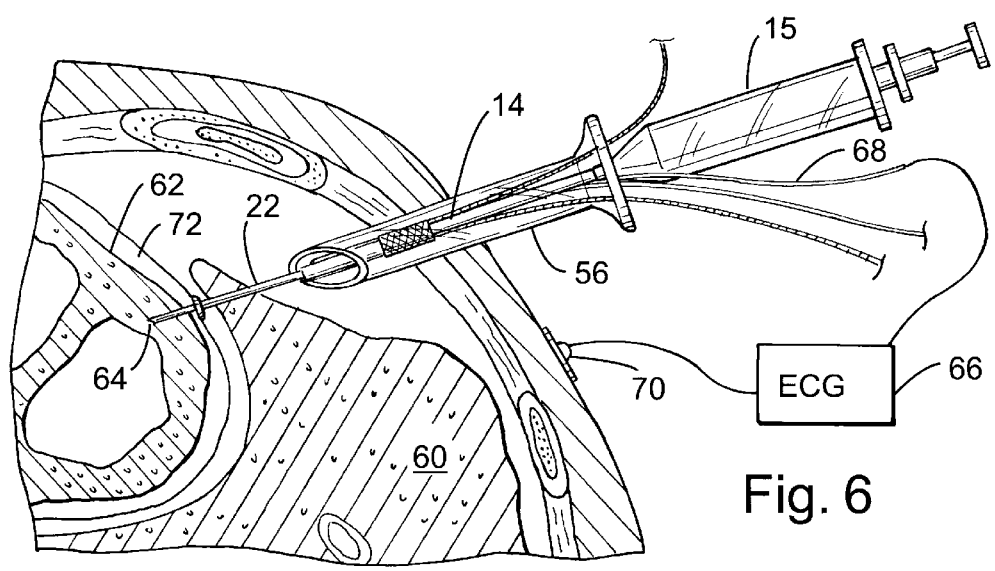
FIG. 6 is an enlarged fragmentary view showing the needle constructed according to teachings of the invention penetrating the lung and heart tissue.

According to another important aspect of the invention, the delivery device 12 is particularly useful when access to heart tissue is obscured by other tissue and cannot be readily separated. For example, in the procedure set forth in International Patent Application WO 99/44656, the patient's lung is collapsed or partially collapsed in order to provide working space in the thoracic cavity. In reoperative patients, however, the lung tissue 60 frequently adheres to the target heart tissue 62, as illustrated in FIG. 6. In accordance with the invention, the needle assembly 14 may be advanced directly through the lung tissue 60 and into the heart tissue 62. In order to facilitate this passage, the smaller diameter needle tip 22 is sufficiently elongated to allow the needle tip 22 to penetrate and advance through the lung tissue 60 and into the cardiac tissue 62. In this regard, the needle tip 22 is preferably on the order of 1½ to 2 inches (approximately 35–50 mm) long. It will be appreciated by those of ordinary skill in the art, however, that the needle tip 22 may be shorter or longer, as conditions warrant.

In order to determine when the needle tip 22 touches or penetrates the cardiac tissue 62, an electrode 64 similar to that disclosed in International Patent Application WO 99/44656, may be provided at the needle tip 22, the remainder of the needle assembly 14 being insulated therefrom. Alternately, the needle tip 22 itself may serve as an electrode if the needle tip 22 is made from a conductive material. Electrical connection of this electrode 64 to an electrocardiograph ("ECG") (schematically illustrated as 66) may be made by running an electrical conductor 68 along the needle assembly 14 to the ECG 66 located outside the patient's body. Standard surface ECG leads 70 are likewise applied to the patient. When the electrode 64 enters the patient's myocardium 62 (see FIG. 6), the event shows as a current injury. In this way, the cardiologist may ensure that the desired positioning and contact is made with the myocardium 62 prior to actuation of the solution supply device 12.

It will be appreciated that the inclusion of the electrode 64 additionally permits the cardiologist to track or electronically mark the injection sites. Accordingly, the cardiologist may follow the marking to ensure that adequate therapeutic solution is applied to the target cardiac tissue to provide optimum conditions for a desired effect. Additionally, such marking facilitates use of the needle assembly 14 in positions that are typically beyond the line of sight provided by way of a surface incision.

It will be further appreciated that alternate marking means and methods may be utilized. For example, markers that may be detected ultrasonographically, radiographically, as, for example, by x-ray or catscan, or electrocardially are appropriate. Virtual marking or mapping may likewise be utilized. Such methods are disclosed, for example, in U.S. application Ser. No. 09/393,873.

According to another important feature of the invention, in order to stabilize the needle assembly 14 during injection, a platform 74 is provided which contacts the surface of the lung tissue 60 or the pericardium 72. To ensure contact of the platform 74 with the tissue and the desired stabilization, the platform 74 is moveable relative to the needle tip 22.

In the embodiment illustrated in FIGS. 5–8, the movable platform 74 is in the form of a collapsible structure. The platform 74 is preferably in the form of an inflatable and deflatable, or collapsible donut-shaped balloon coupled to the periphery of the needle tip 22. A platform 74 on the order of 4–6 mm in diameter when fully inflated is currently considered adequate to provide desired stabilization against tissue. During insertion into the lung or other tissue 60 obstructing access to the heart 62, the platform is fully collapsed against the needle tip 22. In this way, the platform 74 does not interfere with the penetration of the needle tip 22 into and through the lung 60 or other tissue. Rather, the platform 74 passes through the lung 60 or other tissue. The collapsible platform 74 is particularly appropriate when the device 12 is utilized in a true percutaneous technique wherein no incision is made in the chest wall.

Air or other inflating gas is supplied to the platform 74 via an air line 76. The air line 76 extends from a source of gas at its proximal end 78, such as from a compressed gas source or a simple syringe (not shown), along the needle body 20 and needle tip 22, to the platform disposed generally toward the distal end 16 of the needle assembly 14. The deflated, or collapsed, platform 74 is shown in FIG. 7, while the inflated platform is shown in FIG. 8.

The platform 74 is spaced from the distal end 16 of the needle tip 22 to limit the penetration of the needle tip 22 into the cardiac tissue. During use, the collapsed platform 74 is passed through the lung or other obstructing tissue. When the needle tip 22 has penetrated the heart tissue a desired depth, the platform 74 may be inflated to stabilize the needle along the tissue. The platform 74 is preferably inflated, as shown in FIGS. 6 and 8, at a position between the heart tissue 72 or myocardium 62, and the lung tissue 60. In this way, the platform 74 limits the depth to which the needle tip 22 penetrates the cardiac tissue 62. In other words, the platform 74 is preferably spaced from the distal tip 16 of the needle tip 22 a distance equal to the desired needle penetration.

It is presently anticipated that the distal surface of the platform 74 will be disposed on the order of 5–10 mm from the distal tip 45, although alternate spacing may be dictated by factors such as the particular therapeutic solution utilized, or the physical characteristics of the tissue upon which the procedure is to be performed.

In an alternate embodiment of the invention, the movable platform 80 is in the form of a disk which is axially slidable relative to the needle tip 22, as shown in FIGS. 9–11. In this way, the platform 80 may be moved into position against the penetrated tissue at substantially any location along the needle tip 22 in order to stabilize the needle assembly 14 relative to the tissue. In contrast to the movable platform 74 of FIGS. 5–8, which moves by collapsing yet remains stationary relative to the axis of the needle tip 22, the platform 80 of FIGS. 9–11 is movable relative to the axis of the needle tip 22. Further, while the collapsible platform 74 is preferably disposed directly against the heart, the platform 80 steadies the needle tip 22 by placement against the first entered tissue, e.g., the lung tissue.

The platform 80 may be of any appropriate shape or size and formed of any appropriate material. It has been determined that a platform 80 formed of stainless steel and on the order of 4–6 mm in diameter is particularly suitable.

The platform 80 includes a central opening 82 which closely receives the needle tip 22. In order to prevent the platform 80 from separating from the needle tip 22, the needle tip 22 preferably includes an enlarged portion 84. It will be appreciated that the enlarged portion 84 is slightly larger than or presents an interference with the central opening 82 of the platform 80 to prevent the platform 80 from slipping from the end of the needle tip 22. It will further be appreciated that it is not necessary for the enlarged portion 84 to extend about the circumference of the needle tip 22, as is shown. Rather, the enlarged portion 84 need only present sufficient interference to prevent passage of the platform central opening over the enlarged portion 84.

To facilitate proper placement of the platform 80 against the penetrated tissue, a platform adjustment mechanism 86 is provided. In the illustrated embodiment, platform adjustment mechanism is in the form of an adjustment sleeve 86, although an alternate arrangement may be provided. The sleeve 86 is slightly larger than and axially slidably disposed about the needle body 20. In this way, the adjustment sleeve 86 may be manually advanced toward the distal end 16 of the device 12 to contact and move the platform 80 distally and into contact with the tissue. It will be appreciated that the sleeve 86 may likewise be used to position the platform 80 toward the distal end 16 of the needle tip 22 prior to penetration into the tissue. In this way, sleeve 86 moves in the proximal direction as the needle tip 22 penetrates the tissue and the platform 80 contacts the tissue and slides proximally along the needle tip 22. Alternately, the platform 80 may remain in a more proximal location along the needle tip 22 until the needle tip 22 has penetrated the tissue. The sleeve 86 may then be used to advance the platform 80 into contact with the tissue to steady the needle in the tissue.

In order to permit the surgeon to utilize the steering mechanism 40, the steering sleeve 50 preferably is disposed about the platform adjustment sleeve 86, as may best be seen in FIGS. 9 and 10. In this way, the steering sleeve 50 may be advanced along the body 20 to provide the desired bending of the body 20 in conjunction with a tensioning force exerted on the steering cable 42. Additionally, the adjustment sleeve 86 includes a slot 88 for receiving the steering cable 42. Thus, as the platform adjustment sleeve 86 moves axially along the needle body 20, the slot 88 moves along the steering cable 42 such that the sleeve 86 does not interfere with the use of the steering cable 42. It will be appreciated that the platform adjustment sleeve 86 should be fabricated from a material which is sufficiently rigid that it can be pushed axially along the needle body 20 and engage and move the platform 80, yet sufficiently flexible that it can be readily flexed as the device 12 is steered into a desired position for injection. It has been determined that a semi-rigid elastomer or rubber is particularly suitable for this application, although it is envisioned that other materials may be utilized.

In summary, the invention provides a delivery device 12 that may be easily steered into a desired position and utilized for successive injections. The flexibility of the elongated needle body and the versatility of the control mechanism permit the needle to contour the path of delivery to the cardiac and thoracic geometry, providing the cardiologist great latitude in placement of the needle, and precise delivery of the injectant from a remote distance through a relatively small incision. During use, the needle is advanced into position, and the needle tip penetrates the heart tissue, either directly or through adhering lung tissue or other obscuring tissue. An electrode on the needle indicates when the cardiac tissue has been penetrated, and injection site may be marked to ensure injections occurred to desired relative locations. The platform limits the depth of penetration and allows stabilization of the needle against the epicardial surface of the heart or the surface of the lung or other tissue. The solution then can be injected into the cardiac tissue by actuating the syringe. The device is formed of readily available materials and, accordingly, may be economically constructed.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A device for delivering a therapeutic solution from a solution supply into cardiac tissue, the device comprising:

a hollow needle having a needle proximal end and a needle distal end, said needle proximal end being adapted for fluid attachment to said solution supply, said needle comprising an elongated flexible body, and a sharpened tip disposed at said needle distal end for penetration of cardiac tissue, a steering cable having a cable distal end secured to the hollow needle at a coupling, said coupling being spaced from the distal end of the hollow needle, said steering cable extending toward the proximal end of the hollow needle and having a cable proximal end, said steering cable being manipulable to flex the needle distal end relative to the needle proximal end along a flexion radius when a tensioning force is applied to the cable proximal end, and a steering sleeve movable disposed about the elongated flexible body and said steering cable such that a distance between the steering sleeve and said coupling determines the flexion radius and whereby movement of the steering sleeve along the hollow needle adjust the flexion radius.

2. The device as claimed in claim 1 wherein the hollow needle further comprises a platform spaced from the distal end, said platform acting to stabilize the needle relative to the cardiac tissue during delivery of the therapeutic solution.

3. The device as claimed in claim 2 wherein the platform is movable relative to the hollow needle.

4. The device as claimed in claim 3 wherein the platform may slide along the needle.

5. The device as claimed in claim 3 wherein the platform is inflatable.

6. The device as claimed in claim 1 further comprising an electrode coupled to the needle and adapted for connection to an ECG to provide an electrical indication of when said sharpened tip has penetrated said cardiac tissue.

7. The device as claimed in claim 6 wherein the electrode is coupled to the sharpened tip.

8. The device as claimed in claim 3 further comprising an electrode coupled to the needle tip and adapted for connection to an ECG to provide an electrical indication of when said sharpened tip has penetrated said cardiac tissue.

9. The device as claimed in claim 1 further comprising a steering sleeve adjustment cable for adjusting the distance between the steering sleeve and the coupling.

10. The device as claimed in claim 9 wherein the steering sleeve adjustment cable is stainless steel.

11. The device as claimed in claim 9 wherein the steering sleeve adjustment cable is sufficiently resistant to bending that the steering sleeve adjustment cable may be used to push the steering sleeve toward the needle distal end.

12. A device for delivering a therapeutic solution from a solution supply into target tissue, the device comprising:
   a hollow needle having a needle proximal end and a needle distal end, said needle proximal end being adapted for fluid attachment to said solution supply, said needle comprising
      an elongated flexible body,
      a sharpened tip disposed at said needle distal end for penetration of target tissue, and
      a platform moveably disposed along the needle body and spaced from the needle distal end, said platform acting to stabilize the needle relative to the target tissue during delivery of the therapeutic solution.

13. The device as claimed in claim 12 wherein the platform may slide along the needle.

14. The device as claimed in claim 13 further comprising a platform adjustment structure extending adjacent the needle body, said platform adjustment structure being disposed to contact the platform and adjustable to move the platform.

15. The device as claimed in claim 14 wherein the platform adjustment structure is a platform adjustment sleeve disposed about the needle body.

16. The device as claimed in claim 15 wherein the platform adjustment sleeve comprises a slot for receiving the distal end of the steering cable, and the steering sleeve is disposed about the platform adjustment sleeve.

17. The device as claimed in claim 12 wherein the platform is inflatable.

18. The device as claimed in claim 17 further comprising a gas conduit fluidly coupled to the platform and adapted for connection to a source of gas.

19. The device as claimed in claim 12 further comprising an electrode coupled to the needle and adapted for connection to an ECG to provide an electrical indication of when said sharpened tip has penetrated said target tissue.

20. The device as claimed in claim 19 wherein the electrode is coupled to the sharpened tip.

21. The device as claimed in claim 12 further comprising a steering cable having a cable distal end secured to the hollow needle at a coupling, said coupling being spaced from the distal end of the hollow needle, said steering cable extending toward the proximal end of the hollow needle and having a cable proximal end, said steering cable being manipulable to flex the needle distal end relative to the needle proximal end along a flexion radius when a tensioning force is applied to the cable proximal end, a steering sleeve movably disposed about the elongated flexible body and said steering cable such that a distance between the steering sleeve and coupling determines the flexion radius and whereby movement of the steering sleeve along the hollow needle adjusts the flexion radius, and a steering sleeve adjustment cable for adjusting the distance between the steering sleeve and the coupling.

22. The device as claimed in claim 21 wherein the steering sleeve adjustment cable is sufficiently resistant to bending that the steering sleeve adjustment cable may be used to push the steering sleeve toward the needle distal end.

23. A method of delivering a therapeutic substance to heart tissue of a patient, the method comprising:
   inserting a delivery device into the patient's thoracic cavity through an opening in the patient's chest wall, said delivery device having a needle for injecting the therapeutic substance into the heart tissue,
   passing the needle through the patient's lung tissue and into the heart tissue, and
   delivering the therapeutic substance to the patient's heart.

24. The method of claim 23 further comprising the step of at least partially collapsing one of the patient's lungs.

25. The method of claim 23 further comprising the step of providing an indication of when the needle penetrates the heart tissue of the patient.

26. The method of claim 25 wherein the step of providing an indication comprises the step of providing an electrode along the needle, said electrode being electrically connected with a device for indicating when the patient's heart tissue has been penetrated.

27. The method of claim 23 further comprising the steps stabilizing the needle during the delivering step by contacting the lung tissue with a platform disposed about the needle and moving the platform axially relative to the needle as the platform contacts the lung tissue.

28. The method of claim 23 further comprising the steps stabilizing the needle during the delivering step by contacting the cardiac tissue with a platform disposed about the needle.

29. The method of claim 28 wherein the stabilizing step comprises the step of inflating the platform.

30. The method of claim 29 further comprising the step of passing the uninflated platform through the lung tissue.

31. The method of claim 23 further comprising the step of steering the distal end of the needle along a flexion radius using a steering cable coupled to the needle toward the distal end of the needle and extending substantially along the needle.

32. The method of claim 31 further comprising the step of adjusting the flexion radius by moving a steering sleeve disposed about the needle and the steering cable.

33. The method of claim 32 further comprising the step of moving the steering sleeve axially along the needle using a steering sleeve adjustment cable.

34. A method of delivering a therapeutic substance to heart tissue of a patient, the method comprising:

inserting a delivery device into the patient's thoracic cavity through an opening in the patient's chest wall, said delivery device having a needle for injecting the therapeutic substance into the heart tissue, exerting a force on the proximal end of a steering cable, the distal end of the steering cable being coupled to the needle toward the needle distal end to steer the needle distal end along a flexion radius, adjusting the flexion radius by moving a steering sleeve disposed about the needle and the steering cable axially along the needle, the steering cable extending through the steering sleeve such that the proximal end of the steering sleeve is accessible to the user, passing the needle into the heart tissue, and delivering the therapeutic substance to the patient's heart.

35. The method of claim 34 wherein the step of adjusting the flexion radius comprises the step of applying a force to a steering sleeve adjustment cable coupled to the steering sleeve to move the steering sleeve axially along the needle.

36. A method of delivering a therapeutic substance to heart tissue of a patient, the method comprising:

inserting a delivery device into the patient's body cavity through an opening, said delivery device having a needle for injecting the therapeutic substance into the tissue, contacting a sharpened tip of the needle with the heart tissue, penetrating the heart tissue with the sharpened tip, contacting a platform disposed about the needle with body tissue, moving the platform axially relative to the needle, delivering the therapeutic substance to the patient's heart.

37. The method of claim 36 further comprising the step of providing an indication of when the needle penetrates the heart tissue of the patient.

38. The method of claim 37 wherein the step of providing an indication comprises the step of providing an electrode along the needle, said electrode being electrically connected with a device for indicating when the patient's heart tissue has been penetrated.

39. A method of delivering a therapeutic substance to heart tissue of a patient, the method comprising:

inserting a delivery device into the patient's body cavity through an opening, said delivery device having a needle for injecting the therapeutic substance into the tissue, contacting a sharpened tip of the needle with the heart tissue, penetrating the heart tissue with the sharpened tip, inflating a platform disposed adjacent the heart tissue, delivering the therapeutic substance to the patient's heart.

40. The method of claim 39 further comprising the step of passing the needle through lung tissue.

* * * * *